United States Patent [19]

Luteri et al.

[11] Patent Number: 4,546,196

[45] Date of Patent: Oct. 8, 1985

[54] 3-CHLOROBENZYL-3,6-DICHLORO-2-METHOXYBENZOATE

[75] Inventors: George F. Luteri, Mount Prospect; Leonard J. Stach, Riverside; Louis G. Nickell, Chicago, all of Ill.

[73] Assignee: Velsicol Chemical Corporation, Chicago, Ill.

[21] Appl. No.: 619,086

[22] Filed: Jun. 11, 1984

[51] Int. Cl.⁴ ............................................. C07L 69/76
[52] U.S. Cl. ......................................... 560/65; 71/107
[58] Field of Search ........................................... 560/65

[56] References Cited

U.S. PATENT DOCUMENTS

| | | | |
|---|---|---|---|
| 3,013,054 | 12/1961 | Richter | 560/65 |
| 3,600,407 | 8/1971 | Levin et al. | 560/65 |
| 3,619,169 | 11/1971 | Zick | 560/65 |
| 3,767,377 | 10/1973 | Poulos | 560/65 |

FOREIGN PATENT DOCUMENTS 988074  4/1965  United Kingdom .

*Primary Examiner*—Paul J. Killos
*Attorney, Agent, or Firm*—Robert J. Schwarz

[57] ABSTRACT

The subject matter of this application is the new compound, 3-chlorobenzyl-3,6-dichloro-2-methoxybenzoate and its use as a sugarcane ripener.

4 Claims, No Drawings

3-CHLOROBENZYL-3,6-DICHLORO-2-METHOXYBENZOATE

This invention relates to the new compound, 3-Chlorobenzyl-3,6-dichloro-2-methoxybenzoate. It further relates to the use of this new compound to increase the recoverable sugar in sugarcane.

The following demonstrates the preparation of this compound:

EXAMPLE 1

Preparation of 3-Chlorobenzyl 3,6-Dichloro-2-methoxybenzoate

N-Chlorobenzyl alcohol (14.2 grams; 0.1 mol); toluene (100 ml); triethylamine (10.1 grams; 0.1 mol) and dicamba acid chloride (24.0 grams; 0.1 mol) were placed in a 250 ml glass, round bottom flask equipped with stirrer, thermometer, and heating mantle and heated to 75° C. with stirring for five hours. The mixture was cooled to room temperature overnight and the triethylamine hydrochloride filtered from the solution which was then washed twice with 5% hydrochloric acid and twice with water. After being dried over magnesium sulfate, the toluene was removed and the product recrystallized twice from ethanol. The product had a melting point of 39°-41° C.

Elemental Analysis:

|    | Theoretical (%) | Found (%) |
| --- | --- | --- |
| C  | 52.15 | 52.12 |
| H  | 3.21  | 3.18  |
| Cl | 30.78 | 30.67 |

In the use of this compound to increase the recoverable sugar in sugarcane, sugarcane is treated at a late stage of development of the sugarcane wherein most of the sugar formation takes place. Thus, under normal growing conditions and common cultivation practices the active compounds of this invention can be applied to the sugarcane during the period of from about 2 to about 10 weeks before harvesting.

The amount of active compound required to effectively increase the recoverable sugar from sugarcane can vary somewhat depending on such factors as the time of application, the weather, crop density, method of application and the like. Generally, an amount of at least 0.05 pounds per acre and preferably an amount of from 0.05 pounds per acre to about 5 pounds per acre can be used. While an amount greater than those mentioned can be used, they will not result in an advantage that would warrant their expense and are, therefore, not practical.

For practical use in treating sugarcane, the active compound of this invention is generally incorporated into compositions or formulations which comprise an inert carrier and an effective amount of the compound. The compositions enable the active compound to be conveniently applied to the sugarcane at the desired rate. The formulations can be liquid formulations such as emulsifiable concentrates or solutions or solid formulations such as dusts, granules or wettable powders.

The preferred compositions are liquid formulations, particularly solutions or emulsifiable concentrates. Emulsifiable concentrates comprise the active compound, according to this invention, and as the inert carrier, a solvent and an emulsifier. Such emulsifiable concentrates can be extended with water and/or oil to any desired concentration of active compound for application as sprays to the sugarcane. The emulsifier most commonly used in these concentrates are nonionic or mixtures of nonionic with anionic surface-active agents. With the use of some emulsifier systems an inverted emulsion (water-in-oil) can be prepared.

Typical formulations according to the present invention useful for increasing the recoverable sugar in sugarcane are illustrated in the following examples wherein the quantities are given in parts by weight.

EXAMPLE 2

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

3-Chlorobenzyl 3,6-Dichloro-2-Methoxybenzoate—25
Sodium lauryl sulfate—2
Sodium lignin sulfate—3
Kerosene—70

EXAMPLE 3

Preparation of a Wettable Powder

The following components are mixed intimately in conventional mixing or blending equipment and are then ground to a powder having a particle size of less than about 50 microns. The finished powder is dispersed in water to give the desired concentration of active compound for application to the sugarcane.

3-Chlorobenzyl 3,6-Dichloro-2-Methoxybenzoate—50
Fuller's earth—47
Sodium lauryl sulfate—2.5
Methyl cellulose—0.5

EXAMPLE 4

Preparation of a Dust

The following ingredients are mixed thoroughly and are then ground to an average particle size of less than about 50 microns to give a dust suitable for application with conventional dusting equipment.

3-Chlorobenzyl 3,6-Dichloro-2-Methoxybenzoate—10
Powdered talc—90

The effectiveness of the compounds of this invention for increasing the recoverable sugar from sugarcane was demonstrated in a field test by applying a solution in acetone diluted for application to the various indicated application rates. The test compound was applied at each rate on the spindle area of each of 20 stalks of sugarcane in a field in Hawaii, using a syringe with a fine needle as the applicator. A set of 10 of these treated stalks from each group was harvested at 4 and 8 weeks after such treatment. In each harvest a set of 10 untreated stalks were also harvested as a control.

The top 14 joints of the treated cane as well as those of the controls were removed, combined and analyzed for juice purity and pol percent cane, following the "press method" developed and described by T. Tanimoto, Hawaiian Planters Record, 57, 133 (1964). Pol percent cane is a polarimetric determination and equals the percentage of sucrose if the latter is the only substance in the solution which will rotate the plane of polarized light. The pol percent cane is a standard method of determining the sucrose content of sugarcane.

The effectiveness of the compound of this invention for increasing the yield of sugar obtained from sugarcane is demonstrated by the data set out in the following Table. Each experiment represents a separate test conducted at a different time. The cane was harvested 8 weeks after application of the test compound.

TABLE 1

| Experiment Number | | Rate Of Application (Lbs/Acre) | Pol % Cane | Juice Purity |
|---|---|---|---|---|
| 1 | Test Compound | 1.0 | 12.68 | 86.04 |
|   | Control | 0 | 11.48 | 82.21 |
| 2 | Test Compound | 1.0 | 15.07 | 89.31 |
|   | Control | 0 | 9.22 | 72.88 |
| 3 | Test Compound | 0.1 | 10.87 | 79.52 |
|   | Test Compound | 0.05 | 11.87 | 82.87 |
|   | Control | 0 | 9.42 | 77.58 |
| 4 | Test Coopound | 0.5 | 13.47 | 87.15 |
|   | Test Compound | 0.1 | 12.84 | 85.58 |
|   | Control | 0 | 9.52 | 77.12 |
| 5 | Test Compound | 0.5 | 13.97 | 86.52 |
|   | Test Compound | 0.1 | 13.26 | 84.77 |
|   | Control | 0 | 9.98 | 77.32 |
| 6 | Test Compound | 0.5 | 13.22 | 83.82 |
|   | Test Compound | 0.1 | 13.40 | 84.44 |
|   | Control | 0 | 11.61 | 80.66 |
| 7 | Test Compound | 1.0 | 13.33 | 84.92 |
|   | Test Compound | 0.5 | 14.21 | 84.30 |
|   | Test Compound | 0.1 | 12.00 | 81.53 |
|   | Control | 0 | 9.53 | 76.14 |
| 8 | Test Compound | 1.0 | 12.56 | 83.23 |
|   | Test Compound | 0.5 | 14.63 | 88.31 |
|   | Test Compound | 0.1 | 12.96 | 85.97 |
|   | Control | 0 | 11.20 | 81.15 |

In order to demonstrate the unique properties of the present compound, tests were performed on sugarcane plants in accordance with the foregoing procedures using other substituted benzyl esters of dicamba. The results of these tests in comparison to the results obtained using the present compound are reported in the following table using the following test scale:

— = Negative effect
0 = No effect
1 = Low level effect
2 = Moderate effect
3 = Commercial level effect
4 = Above commercial level effect
N.T. = No test

TABLE 2

| Substituent | Position of Substituent | | |
|---|---|---|---|
|  | Ortho | Meta | Para |
| Nitro | 1* | — | —* |
| Chloro | 2* | 4 | 0* |
| Bromo | 0 | — | — |
| Fluoro | NT | NT | 1 |
| Methyl | 2 | 0 | — |
| Methoxy | 0 | 2 | — |

The results represent two tests for each compound except for the compounds identified with an * which represents three tests and the claimed compound (meta-chloro) which represents 30 tests.

We claim:

1. The compound, 3-Chlorobenzyl 3,6-Dichloro-2-Methoxybenzoate.

2. A method for increasing the recoverable sugar contained in sugarcane which comprises contacting the sugarcane plant with an effective amount of the compound of claim 1.

3. The method of claim 2 wherein the sugarcane is contacted with from about 0.05 to about 5 pounds per acre of the compound of claim 1.

4. The method of claim 2 wherein the sugarcane is contacted with the compound of claim 1 during the period of from about 2 to about 10 weeks before harvest.

* * * * *